United States Patent [19]

Bertrand et al.

[11] Patent Number: 4,938,416

[45] Date of Patent: Jul. 3, 1990

[54] METHOD OF DELIVERING A WATER-BASED ROOM AIR FRESHENER

[75] Inventors: Jerome C. Bertrand, Woodside, Calif.; Robert Pirolo, Tacoma, Wash.

[73] Assignee: Consoldiated Ceramic Products, Inc., Blanchester, Ohio

[21] Appl. No.: 352,563

[22] Filed: May 16, 1989

[51] Int. Cl.⁵ .................. B05B 9/043

[52] U.S. Cl. .................. 239/1; 239/333

[58] Field of Search .................. 239/1, 333, 331, 329; 222/383

[56] References Cited

U.S. PATENT DOCUMENTS

| | | | |
|---|---|---|---|
| Re. 283,366 | 3/1975 | Pechstein | 239/333 |
| 2,422,145 | 6/1947 | Taylor | 99/140 |
| 4,051,983 | 10/1977 | Anderson | 222/321 |
| 4,184,985 | 1/1980 | Scheuermann et al. | 252/522 |
| 4,250,165 | 2/1981 | Foley | 424/76 |
| 4,264,478 | 4/1981 | Seldner | 252/522 |
| 4,803,195 | 2/1989 | Holzner | 512/4 |

*Primary Examiner*—Andres Kashnikow

*Assistant Examiner*—Karen B. Merritt

*Attorney, Agent, or Firm*—Wood, Herron & Evans

[57] ABSTRACT

A method of delivering a water-based room air freshener is disclosed that provides a hand held pump sprayer to deliver a minute amount of atomized particles into the room atmosphere for immediate detection by the olfactory senses. The water-based disprsions include about 88% to about 99% by weight water, about 0.1% to about 5% by weight fragrance oil, about 0.1% to about 5% by weight surfactant, and about 0.1% to about 2% by weight preservative, with the dispersions preserved against microbial attack and free from volatile propellants.

14 Claims, No Drawings

METHOD OF DELIVERING A WATER-BASED ROOM AIR FRESHENER

BACKGROUND OF THE INVENTION

A variety of air treating or air freshener products have been developed for commercialization. Among those that are being marketed include the liquid-wick products, solid air-treating agents and aerosols. With liquid-wick and solid air-treating products, the volatile fragrance slowly vaporizes when the liquid-wick or solid is exposed to air. In the case of aerosols, chlorofluorocarbons, short-chain hydrocarbons, short-chain alcohols, and carbon dioxide are employed as solvents and/or propellants to spray the fragrance into the atmosphere. A number of problems are associated with each of these products. First, with respect to liquid-wick or solid air-treating products, the rate of release of the active ingredients is not uniform and usually diminishes with time. Furthermore, these products do not last very long due to the rapid evaporation of volatile fragrance components . Aerosol compositions have proved detrimental to the ozone/oxygen balance in the Earth's upper atmosphere. Accordingly, while the sale of air fresheners has expanded substantially, there is a need for improved products where lasting fragrance levels may be produced economically. Furthermore, there is the need to eliminate products that provide undesirable components such as propellants that are detrimental to the Earth's atmosphere or are otherwise ecologically unsafe.

SUMMARY OF THE INVENTION

This invention is directed to a method of delivering a water-based room air freshener that overcomes the problems associated with currently available products. In particular, this invention is directed to a method of delivering a water-based room air freshener by introducing into the air a measured minute amount of atomized particles such that a fragrance oil is atomized and released into the air for immediate detection by the olfactory senses.

The water-based composition suitable for use in this invention is a liquid dispersion, emulsion or solution of a fragrance oil and surfactant in water. The dispersion is preserved against microbial attack and potential deterioration and malodor development by a proper formulation of ingredients. Importantly, the water-based fragrance dispersions of this invention are free from volatile propellants/solvents of the chlorofluorocarbon, short-chain hydrocarbon, short-chain alcohol or carbon dioxide type. These dispersions are delivered by a pump sprayer having a liquid container that is adapted to deliver a measured minute amount of atomized particles of the liquid dispersion into a room upon manual activation of the pump. The pump usually has a piston that is activated by the index finger of a hand and upon activation the measured minute amount of atomized particles of the water-based fragrance liquid is dispensed into the air.

It has been found quite surprisingly that water-based fragrance compositions may be formulated, maintained and delivered in a measured atomized state to provide an immediate blossoming effect of fragrance that may be detected by the olfactory senses. This has been dramatically demonstrated by employing a pump sprayer that is adapted to deliver a minute amount of liquid on the order of about 0.1 to 0.2 cc into the atmosphere of a room. Upon the delivery of such a minute amount, employing the water-based fragrance compositions of this invention, the fragrance tends to immediately blossom. The exact reasoning for this effect is unknown, but it is theorized that the atomization of the water-based fragrance liquid tends to disrupt the oil and water phases such that the fragrance oil is released into the atmosphere for detection by the olfactory senses. There is a slight delay on the order of several seconds for the olfactory senses to detect the fragrance. For instance, if one were in the room after such a minor amount of fragrance solution is atomized, even if one were within 15-°feet of such an atomization, the olfactory senses pick up the blossoming effect of the fragrance within seconds. No propellants are involved in this technique. Surprisingly, mechanical atomization of the water-based fragrance dispersions in such minute amounts provide a long lasting fragrance effect in the room atmosphere for up to several hours.

The results of this invention, when contrasted with the prior art air fresheners currently available, are very advantageous. As mentioned, with the elimination of any volatile solvents, any detrimental effects attributable to such solvents of the chlorofluorocarbon or short-chain alcohol or short-chain hydrocarbon type are eliminated. Accordingly, there is no negative impact caused by the water-based fragrance upon the ozone/oxygen balance in the Earth's upper atmosphere; and the pump spray delivery of this invention requires no carbon dioxide pressurization or flammable propellant. Rather, water-based fragrance dispersions when sprayed into the air provide brilliantly fresh and pleasant fragrance effects.

In another aspect of this invention, it has been found that very low levels of fragrance oils in a predominantly water-based composition provide the desired results. More specifically, fragrance levels on the order of 0.1–0.5% by weight in 96–97.5% water provide the desired effect. This indeed is surprising especially when only about 0.1–0.2 cc of liquid may be atomized in the room. More generally, compositions of this invention on a percent by weight basis comprise about 88–99% water, about 0.1–5% fragrance oil, about 0.1–5% surfactant and, optionally when needed, 0.1–2% preservative. More preferable ranges include about 96–97.5% water, about 0.1–2% fragrance oil, about 0.1–2% surfactant and, optionally, about 0.1–2% preservative. Only a measured minute amount of atomized water-based fragrance liquid of about 0.1 to 0.2 cc needs to be dispensed into the atmosphere of an ordinary room size of 10×15 feet to about 20×20 feet. Of course, when desired or in larger rooms, it may be necessary to pump more than one stroke of atomized fragrance liquid into various parts of the room to freshen the air.

In contrast to the liquid-wick or solid type air fresheners that do not last very long and lack uniform aromatic release, the water-based fragrance atomization of this invention provides for long lasting effects of up to several hours in a room with delivery of only such a minute amount of about 0.15 cc of liquid. Therefore, one may achieve months of air freshening from an equivalent weight amount of atomized liquid as compared to the liquid or solid type air fresheners currently available which frequently last for no more than several days. This is a significant value attributable to the method of delivery according to the principles of this invention. The water-based systems are ecologically safe in contrast to the currently available aerosols that are based upon flammable alcohols or other hydrocarbon propellants.

The above enumerated advantages and other advantages will be understood with reference to the further detailed description hereinafter

DETAILED DESCRIPTION

The water-based fragrance dispersions of this invention contain almost all water as indicated above on the order of about 88–99% by weight, preferably about 96–97.5%. The fragrance oil containing compositions are those that are well known and formulated by skilled perfumers/fragrance chemists. These fragrance oil compositions are usually well balanced, complex mixtures. Thus, the term "fragrance oil" is used in this description and in the claims to define a fragrance oil or essence that is solubilized, emulsified, or otherwise dispersed throughout the water matrix usually by a surfactant or similar compatibilizing compound. The fragrance oil usually is oleophilic and needs an assist for compatibilization by emulsification, dispersion or solubilization in water. Accordingly, all conventional fragrances that are constituted by volatile or odorous agents, including essential oils and aroma chemicals that are known to those skilled in the perfumery and fragrance arts may be employed under the term "fragrance oil" herein. They usually comprise one or more natural materials or synthetic aroma chemicals or mixtures of the two. Some examples of natural fragrances are citronellol, hydroxy-citronellol, rhodinol, eugenol, geraniol, rose oil, heliotropine, peru balsam, ylang-ylang oil, isoeugenol, bergamot, coumarin, musk, and all or any of the "synthetic" counterparts of the foregoing, and aroma chemicals of which there is no counterpart in nature. These materials are generally used in combination to achieve the desired fragrance and odor counteractant effect. Other fragrance enhancers in trace amounts may be employed such as selected alcohols, esters, ketones, aldehydes, acids, terpenes, ethers and other materials of a highly complex nature, to name a few. These trace materials function only as odorants and not as propellants because they are only present in such trace amounts. Essential oils (volatile oils) are found in plants and are usually defined as more or less volatile materials isolated by a physical process. Flower oils, and oleo-based resins are usually only partially volatile and therefore only partly contain essential oils. Animal secretions and extracts of this general class of essential oils are either derived, for instance, from glands of the male musk deer (natural musk), or by other accumulated materials in the animals that are not classified as a gland secretion. Macrocyclic musks can also be chemically synthesized. Compounds like macrocyclic ketones or lactones that may also include indans and tetralins, derivatives of hydrindacene, isochroman, naphthidan, and coumarin. Of course, low volatility solvents may be employed to assist in the formation of a balanced fragrance oil as that term is used herein and including such solvents as dipropylene glycol and benzyl benzoate. It will therefore be understood in accordance with the teachings of this invention that there are many fragrance oils that may be formulated into the desired water-based fragrance oil and delivered in accordance with the principles of this invention. Examples of fragrance oils or compositions that may be derived from the patent art are disclosed in U.S. Pat. Nos. 2,422,145; 4,184,985; 4,250,165; 4,264,478 and 4,803,195, and these patents are incorporated herein by reference.

The surfactant component of the water-based fragrance compositions of this invention is preferably of the nonionic type and includes particularly polyoxyethylene phenols or fatty acid esters. In particular, surfactants such as nonylphenol polyoxyethylene (100) manufactured by Rohm & Haas under the mark TRITON X-100 or polyoxyethylene (20) sorbitan monooleate manufactured by ICI under the mark TWEEN 20 are examples of suitable nonionic surfactants. Other nonionic surfactants or emulsifying agents are well known in the art and, again with reference to the above identified patents that are incorporated herein by reference, any of such surfactants may be employed to formulate the water-based fragrance liquid solutions, emulsions or more generically dispersions of this invention. The amount of the surfactant is usually about the same as the fragrance oil composition, i.e., namely on the order of about 0.1 to about 5% by weight, most preferably about 0.1 to about 2% by weight to compatibilize the water and oil phase into a stable dispersion. Certain surfactants also provide a biologically stabilizing or preservative effect. However, other preservatives or additives may be included in the composition to prevent the composition from deterioration either by bacteriological or related means. A preferred preservative is phenoxyethanol. Other preservatives along with other additives may be employed in the water-based fragrance compositions of this invention as such are disclosed in the above identified patents and such disclosures are incorporated herein by reference.

The pump sprayer that is suitable for use in accordance with the principles of this invention is disclosed is U.S. Reissue Pat. No. 28,366 and U.S. Pat. No. 4,051,983. It has been found that a pump sprayer of the type disclosed in these patents having a liquid container may be adapted to deliver a measured minute amount of atomized particles of the water-based fragrance dispersions of this invention. Water-based fragrance oil dispersions containing surfactant, free from volatile propellants, may be dispensed from such a pump sprayer by manually activating the pump to deliver a measured minute amount of atomized particles of the fragrance liquid for freshening the air. Upon atomization of the water-based fragrance liquid, there is a release of the fragrance into the air, thereby freshening the room with the aroma of the fragrance. Such an aroma is rather immediately detected by the olfactory senses. The above pump sprayer is capable of delivering atomized particles where 97% by particle count are in the range of about 1 to 10 microns and this amounts to about 3% by weight of the total liquid that is delivered by a single stroke of the pump. The 97% by weight balance of particles that are atomized are greater than about 10 microns. Importantly, measured minute amounts on the order of about 0.1 to about 0.5 cc, preferably about 0.1 to about 0.2 cc, are delivered using such a pump spray. Of course, greater amounts may be delivered per stroke if desired, but large amounts are not considered necessary.

The following are operating examples illustrate the invention employing the pump sprayer just described with a composition that falls within the following general formula on a percent by weight basis:

| | |
|---|---|
| Water | 96–97.5% |

-continued

| | |
|---|---|
| Surfactant | 0.5–2% |
| Fragrance Oil | 0.5% |
| Preservative | 1.5% |

In the above general formula, the surfactants employed include nonylphenol polyoxyethylene (100), identified above as TRITON X-100 and polyoxyethylene (20) sorbitan monooleate identified above as TWEEN 20. The preservative employed is phenoxyethanol. Using these identified surfactants and preservative, the following fragrance oils were formulated in the above general formula and atomized:

| FRAGRANCE OIL | CUSTOM ESSENCE CONTROL NO. |
|---|---|
| Ozone Air | CE-6039 |
| Ozone Fresh | CE-6040 |
| Forest Fresh | CE-6041 |
| Springtime | CE-6042 |
| Ozone Fresh | CE-6170 |
| Fresh & Clean | CE-6171 |
| Fresh & Lite | CE-6172 |
| Peach | CE-5626 |
| Obsession type | CE-6216 |
| Obsession (Women's) type | CE-6217 |
| Powder Fresh | CE-6218 |
| Giorgio type | CE-6405 |
| Poison type | CE-6406 |
| Oscar type | CE-6407 |
| White Linen type | CE-6408 |
| Rose | CE-6446 |
| Citrus Bouquet | CE-6447 |
| Evergreen | CE-6448 |
| Apple Pie | CE-6449 |
| Powder Puff | CE-6450 |
| Peach | CE-6451 |
| Floral Bouquet | CE-6452 |
| Fresh Unisex | CE-7106 |
| Nature Fresh | CE-7107 |
| Forest Edge | CE-7108 |
| Anais-Anais type | CE-7025 |
| Chanel #5 type | CE-7020 |

All of the above fragrances have been produced by Custom Essence, Inc. of Somerset, N.J. and have been designated by the Custom Essence control number. As is well understood in the art, fragrance oils of the above type have many, perhaps hundreds of chemical components, and such are contained usually in only trace amounts. The precise formulas of these fragrance oils are trade secrets of others and such do not form a part of this invention.

When aqueous-based fragrance compositions employing the above fragrances were formulated with the surfactants and preservative within the range of the compositional percents by weight, and such compositions were atomized with the above disclosed pump sprayer, a single pump delivered approximately 0.15 cc, or within the range of 0.1–2 cc, of atomized particles of the water-based fragrance liquid whereupon there was released into the air an aroma of the fragrance that was immediately detected by the olfactory senses. A single pump into an average size room provides an aroma almost immediately detected and long lasting for up to hours. Spraying such a minute amount surprisingly provides a brilliantly fresh and pleasant fragrance even at the low percentages of fragrance loadings identified above. It is to be noted that the air freshener compositions according to the above examples utilize fragrance oils that are virtually free of any isopropyl or ethyl alcohol or other solubilizing short-chain alcohols, or other flammable propellants such as volatile hydrocarbons or the chlorofluorocarbons that are detrimental to the ozone/oxygen balance in the Earth's atmosphere. The compositions above are solubilized or emulsified in water using the low-odor surfactant and are preserved against bacteria, yeast or fungus attack by the phenoxyethanol preservative. Furthermore, the pump sprayer requires no carbon dioxide pressurization. It is simply actuated by finger pressure exerted by the mechanical pump.

Having described the invention and examples of water-based fragrance liquids that may be delivered according to the method of this invention, and a suitable pump sprayer, it will be understood that variations in formula, components and methods of delivery may be made all within the scope of this invention.

What is claimed is:

1. A method of delivering a water-based room air freshener comprising providing a pump sprayer having a liquid container adapted to deliver a minute amount of atomized particles of said liquid into the room atmosphere upon manually activating the pump, providing in said sprayer container a liquid comprising a water-based dispersion of a fragrance oil and surfactant, said dispersion preserved against microbial attack and free from volatile propellant, and manually activating said pump to deliver a minute amount of atomized particles of said liquid into the room air, said fragrance oil being released upon said atomization for immediate detection by the olfactory senses.

2. The method of claim 1 wherein said liquid comprises about 88 to about 99% by weight of water, about 0.1 to about 0.5% by weight fragrance oil and a surfactant in an effective amount to compatibilize said water and oil phases into a stable dispersion.

3. The method of claim 1 wherein said liquid comprises about 88 to about 99% by weight of water, about 0.1 to about 5% fragrance oil and about 0.1 to about 5% by weight surfactant.

4. The method of claim 3 wherein said liquid further contains a preservative in an amount of about 0.1 to about 2% by weight.

5. The method of claim 1 wherein said surfactant is selected from the group consisting of a polyoxyethylene fatty acid ester and polyoxyethylene alkylphenol.

6. The method of claim 5 wherein a surfactant is polyoxyethylene sorbitan monooleate or nonylphenolpolyoxyethylene.

7. The method of claim 4 wherein said preservative is phenoxyethanol.

8. A method of delivering a water-based room air freshener comprising providing a hand-held pump sprayer having a liquid container adapted to deliver a minute amount of atomized particles of said liquid into the room atmosphere upon hand activating the pump, providing in said sprayer container a liquid comprising a water-based dispersion of about 88% to about 99% by weight water, about 0.1% to about 2% by weight fragrance oil, about 0.1% to about 2% by weight surfactant, and about 0.1% to about 2% by weight preservative, said dispersion preserved against microbial attack and free from volatile propellant, hand activating said pump to deliver a measured minute amount of atomized particles of said liquid into the room air, said fragrance oil being released upon said atomization for immediate detection by the olfactory senses.

9. The method of claim 8 wherein the measured amount of atomized particles is on the order of about 0.1 to about 0.5 cc.

10. The method of claim 8 wherein the measured amount of atomized particles is on the order of about 0.1 to about 0.2 cc.

11. The method of claim 8 wherein said liquid comprises about 96 to about 97.5% by weight of water, about 0.1 to about 0.5% fragrance oil and about 0.1 to about 0.5% by weight surfactant.

12. The method of claim 8 wherein said surfactant is selected from the group consisting of a polyoxyethylene fatty acid ester and polyoxyethylene alkylphenol.

13. The method of claim 12 wherein said preservative is phenoxyethanol.

14. A method of delivering a water-based room air freshener comprising providing a hand-held pump sprayer having a liquid container adapted to deliver a minute amount of atomized particles of said liquid into the room atmosphere upon hand activating the pump, providing in said sprayer container a liquid comprising a water-based dispersion of about 96% to about 97.5% by weight water, about 0.1% to about 0.5% by weight fragrance oil, about 0.1% to about 0.5% by weight surfactant selected from the group consisting of polyoxyethylene fatty acid ester and polyoxyethylene alkylphenol and about 0.1% to about 2% by weight phenoxyethanol, said dispersion preserved against microbial attack and free from volatile propellant, hand activating said pump to deliver a measured minute amount of about 0.1 to about 0.2 cc of atomized particles of said liquid into the room air, said fragrance oil being released upon said atomization for immediate detection by the olfactory senses.

* * * * *